(12) United States Patent
Haik et al.

(10) Patent No.: US 7,842,281 B2
(45) Date of Patent: Nov. 30, 2010

(54) MAGNETIC PARTICLE COMPOSITION FOR THERAPEUTIC HYPERTHERMIA

(75) Inventors: Yousef Haik, Tallahassee, FL (US); Ching-Jen Chen, Tallahassee, FL (US)

(73) Assignee: The Florida State University Research Foundation, Tallahassee, FL (US)

( * ) Notice: Subject to any disclaimer, the term of this patent is extended or adjusted under 35 U.S.C. 154(b) by 1515 days.

(21) Appl. No.: 11/125,488

(22) Filed: May 10, 2005

(65) Prior Publication Data

US 2005/0249817 A1 Nov. 10, 2005

Related U.S. Application Data

(60) Provisional application No. 60/569,726, filed on May 10, 2004.

(51) Int. Cl.
*A61B 5/055* (2006.01)
*A61M 37/00* (2006.01)
*B32B 5/16* (2006.01)
*H01F 1/00* (2006.01)
*A61K 33/24* (2006.01)

(52) U.S. Cl. .......................... 424/9.3; 607/105; 600/12; 128/898; 252/62.54; 428/407; 424/617

(58) Field of Classification Search ........................ None
See application file for complete search history.

(56) References Cited

U.S. PATENT DOCUMENTS

| | | | |
|---|---|---|---|
| 4,654,267 A | | 3/1987 | Ugelstad et al. |
| 4,774,265 A | | 9/1988 | Ugelstad et al. |
| 4,861,627 A | | 8/1989 | Mathiowitz |
| 5,720,961 A | | 2/1998 | Fowler et al. |
| 5,763,203 A | | 6/1998 | Ugelstad et al. |
| 5,874,029 A | | 2/1999 | Subramaniam et al. |
| 5,916,539 A | * | 6/1999 | Pilgrimm ................. 424/9.322 |
| 5,985,312 A | | 11/1999 | Jacob et al. |
| 6,048,515 A | | 4/2000 | Kresse et al. |
| 6,129,848 A | | 10/2000 | Chen et al. |
| 6,143,211 A | | 11/2000 | Mathiowitz et al. |
| 6,632,671 B2 | | 10/2003 | Unger |
| 2003/0086867 A1 | | 5/2003 | Lanza et al. |
| 2003/0146529 A1 | | 8/2003 | Chen et al. |
| 2004/0065969 A1 | | 4/2004 | Chatterjee et al. |

OTHER PUBLICATIONS

Upadhyay, T. et al., "Thermomagnetic behaviour of Gd substituted ferrite magnetic fluids", 2002, Indian Journal of Pure and Applied Physics, 40, 282-289.*
Rath, C., et al., "Dependence on cation distribution of particle size, lattice parameter, and magnetic properties in nanosize Mn-Zn-ferrite", 2002, Journal of Applied Physics, 91(4), pp. 2211-2215.*
Kikukawa, N., et al., "Preparation of Spinel-Type Ferrite Fine Particles via Plasma Route Using Amorphous Citrate Gel as a Precursor", 2002, Japan Journal of Applied Physics, 41, pp. 5991-5992.*

Parekh, K., et al., "Electron spin resonance study of a temperature sensitive magnetic fluid", 2000, Journal of Applied Physics, 88(5), pp. 2799-2804.*
Kuznetsov, A.A., et al., "Smart Mediatiors for Self-Controlled Inductive Heating", 2002, European Cells and Materials, 3(2), pp. 75-77.*
Auzans, et al., "Properties of Mn-Zn ferrite nanoparticles for aqueous ferrofluids," *Magn. Gidrodinamika* , 38:78-86 (1999). Abstract.
Auzans, et al., "Synthesis and properties of Mn-Zn ferrite ferrofluids," *J. Mater. Sci.*, 34:1253-60 (1999).
Auzans, "Mn-Zn ferrite nanoparticles for water- and hydrocarbone-based ferrofluids: preparation and properties," Thesis (1999).
Belc, et al., "Effect of High AC Magnetic Field on Magnetic Nanoparticles for Magnetic Hyperthermia and Radiation/Chemotherapy Applications," http//www.nsti.org/Nanotech2005/showabstract.html?absno=243 (2005). Abstract.
Berkovsky, et al., *Magnetic Fluids, Engineering Applications*, pp. 48-50, 203-10, Oxford University Press, (1993).
Billi, et al., "Ionizing-Radiation Resistance in the Desiccation-Tolerant Cyanobacterium *Chroococcidiopsis*," *Appl. & Environm. Microbiology*, 66:1489-92 (2000).
Brady, et al., Eds., "Materials Handbook $14^{th}$ edition," pp. 36-40, 582-89, McGraw-Hill Professional, 2002.
Burns, *Solid State Physics*, pp. 317-21, Academic Press Inc. (1985).
Chan, et al., "Synthesis and evaluation of colloidal magnetic iron oxides for the site-specific radiofrequency-induced hyperthermia of cancer," *J. Magn. Mater.*, 122:374-78 (1993).
Childress, et al., "Granular Fe in a metallic matrix," *Appl. Phys. Lett.*, 56:95-97 (1990).
Gilleo, "Ferromagnetic Insulators: Garnets" in *Ferromagnetic Materials*, pp. 34-35 (North Holland Physics Publishing, 1980).
Guo, et al., "Preparation and Dispersion of Ni-Cu Composite Nanoparticles," *Phys. Chem. Chem. Phys.*, 4:3422-24 (2002).
Hergt, "Physical Limits of Hyperthermia Using Magnetite Fine Particles," *IEEE Transactions on Magnetics*, 34(5):3745-54 (1998).

(Continued)

*Primary Examiner*—Michael G Hartley
*Assistant Examiner*—Lance Rider
(74) *Attorney, Agent, or Firm*—Sutherland Asbill & Brennan LLP

(57) ABSTRACT

Magnetic nanoparticle compositions are provided which provide an inherent temperature regulator for use in magnetic heating, particularly for use in magnetic hyperthermia medical treatments. The composition includes magnetic nanoparticles having a Curie temperature of between 40 and 46° C., preferably about 42° C., and may further include a polymeric material and optionally a drug or radiosensitizing agent. Methods of hyperthermia treatment of a patient in need thereof are provided which include the steps of administering to the patient a composition comprising magnetic nanoparticles having a Curie temperature of between 40 and 46° C.; and exposing the magnetic nanoparticles in the patient to an alternating magnetic field effective to generate hysteresis heat in the nanoparticles.

8 Claims, 13 Drawing Sheets

OTHER PUBLICATIONS

Herzer, "Nanocrystalline soft magnetic materials," *J. Magnetism & Magn. Mater.*, 112:258-62 (1992).

Hofer, "Hyperthermia and Cancer," 4$^{th}$ *Int. Conf. Scientific and Clinical Applications of Magnetic Carriers*, Tallahassee-FL, pp. 67-69 (2002).

Hofer, et al., "Effect of Hyperthermia on the Radiosensitivity of Normal and Malignant Cells in Mice," *Cancer*, 38:279-87 (1976).

Jordan, et al., "Magnetic fluid hyperthermia (MFH): Cancer treatment with AC magnetic field induced excitation of biocompatible superparamagnetic nanoparticles," *J. Magnetism & Magn. Mater.*, 201:413-19 (1999).

Jordan, et al., "Endocytosis of dextran and silan-coated magnetite nanoparticles and the effect of intracellular hyperthermia on human mammary carcinoma cells in vitro," *J. Magnetism & Magn. Mater.*, 194:185-96 (1999).

Jordan, et al., "Cellular uptake of magnetic fluid particles and their effects on human adenocarcinoma cells exposed to AC magnetic fields in vitro," Int. *J. Hyperthermia*, 12:705-22 (1996).

Kinnari, et al., "Magnetic properties of Fe-Zn ferrite substituted ferrofluids," *J. Magnetic & Magn. Mater.*, 252:35-38 (2002).

Kittel, *Intro. To Solid State Physics* 8, pp. 550-51 (John Wiley & Sons, NY, 4m Ed.), 1971.

Koch, "The synthesis and structure of nanocrystalline materials produced by mechanical attrition: A review," *Nanostructured Mater.*, 2:109-29 (1993).

Koch, "Materials Synthesis by Mechanical Alloying," *Annu. Rev. Mater. Sci.*, 19:121-43 (1989).

Koch, "Top-down synthesis of nanostructured materials: Mechanical and thermal processing methods," *Rev. Adv. Mater. Schi.*, 5:91-99 (2003).

Kolekar, et al., "The effect of $Gd^{3+}$ and $Cd^{2+}$ substitution on magnetization of copper ferrite," *J. Magnetism & Magn. Mater.*, 247:142-46 (2002).

Kubo, et al., Eds., *Solid State Physics*, pp. 450-52 (McGraw Hill 1969).

Kuznetsov, et al., "Smart mediators for self-controlled inductive heating," *Eur. Cells Mater.*, 3:75-77 (2002).

Leslie-Pelecky, et al., "Magnetic Properties of nanostructured materials," *Chem. Mater.*, 8:1770-83 (1996).

Lilly, et al., "Hyperthermia induction with thermally self-regulated ferromagnetic implants," *Radiology*, 154:243-44 (1985).

Natter, et al., "Nanocrystalline nickel and nickel-copper-alloys: Synthesis, characterization and thermal stability," *J. Mater. Res.*, 13:1186-97 (1998).

Pal, et al., "Nanocrystalline magnetic alloys and ceramics," *Sadhana* 28:283-97 (2003).

Pankhurst, et al., "Applications of magnetic nanoparticles in biomedicine," *Phys. D: Appl. Phys.*, 36:R167-R181 (2003).

Schneiderman, et al., "Targets for Radiation-Induced Cell Death: When DNA Damage Doesn't Kill," *Radiat. Res.* 155:529-35 (2001).

Schröder, *Electronic, Magnetic, and Thermal Properties of Solid Materials*, pp. 195-196, 218 (Marcel Dekker Inc. NY, 1978).

Smit, et al., *Ferrites*, pp. 139-142 (John Wiley & Sons, NY, 1959).

Upadhyay, et al., "Gd-substituted ferrite ferrofluid: a possible candidate to enhance pyromagnetic coefficient," *J. Magnetic & Magn. Mater.*, 201:129-32 (1999).

Vassiliou, et al., "Magnetic and optical properties of $\gamma$-$Fe_2O_3$ nanocrystals," *J. Appl. Phys.*, 73:5109-16 (1993).

* cited by examiner

MAGNETIC PARTICLE COMPOSITION FOR THERAPEUTIC HYPERTHERMIA

CROSS-REFERENCE TO RELATED APPLICATIONS

This application claims the benefit of U.S. Provisional Application No. 60/569,726, filed May 10, 2004. The application is incorporated herein by reference in its entirety.

BACKGROUND OF THE INVENTION

This invention relates generally to magnetic nanoparticle compositions, and more particularly to magnetic nanoparticle compositions useful in self-controlled hyperthermia treatment.

Diseases of the human body such as malignant tumors are generally treated by excision, chemotherapy, radiotherapy or a combination of these approaches. Each approach has limitations affecting it clinical utility. For example, excision may not be appropriate where the disease presents as a diffuse mass or is in a surgically inoperable location. Chemotherapeutic agents are generally non-specific, thus resulting in the death of both normal and diseased cells. Radiotherapy is also nonspecific and results in the death of normal tissues exposed to ionizing radiation. In addition, some diseases such as tumors, particularly the core of a tumor mass, may be relatively resistant to ionizing radiation or chemotherapeutic agents.

Hyperthermia has been proposed as a cancer treatment, and published evidence confirms that hyperthermia is effective in treating diseases like cancerous growths. It is understood that malignant cells are reliably more sensitive to heat than normal cells. The therapeutic benefit of hyperthermia therapy is mediated through two principal mechanisms: (1) a directly tumoricidal effect on tissue by raising temperatures to greater than 42° C., resulting in irreversible damage to cancer cells; and (2) hyperthermia sensitizes cancer cells to the effects of radiation therapy or to certain chemotherapeutic drugs. The lack of any cumulative toxicity associated with hyperthermia therapy, in contrast to radiotherapy or chemotherapy, further suggests the desirability of developing improved systems for hyperthermia therapy. While considerable success has been observed in treating superficial tumors using hyperthermia therapy, there remains a need for a method of selectively targeting and treating diseased tissue in a patient.

A large fraction of a tumor's mass is made of hypoxic (poorly oxygenated) cells. Hypoxic cells are much more resistive to radiation therapy than euoxic (well oxygenated) cells. It has been reported that when heat and a radiosensitizing agent (e.g., misonidazole) are used in combination with each other, they produce synergistic potentiation effects. See Schneiderman, et al., $Radiat. Res.$ 155:529-35 (2001); Billi, et al., $Appl. \& Environm. Microbiology$ 66: 1489-92 (2000); and Hofer, "Hyperthermia and Cancer," $4^{th}$ $Int. Conf. Scientific and Clinical Applications of Magnetic Carriers$, Tallahassee-Fla., pp. 78-80 (2002). In Hofer's report, hypoxic cancer cells subjected to the two agents during irradiation showed a response enhanced by a factor of 4.3, which far exceeded the euoxic cells. However, Hofer's whole body heating approach is not optimal for clinical application on human, because whole-body heating limits the heat dose that can be given. It would be more desirable to provide a combination therapy in which only the tumor region is heated, i.e., selective hyperthermia.

Clinical feasibility of treating cancer by hyperthermia alone has been investigated (Jordan, et al., $2nd Int. Conf.$ $Scientific and Clinical Applications of Magnetic Carriers$, Cleveland-Ohio, 29 (1998); Hofer et al., $Cancer$ 58: 279-87 (1976)). Limitations of these methods are due either to the invasive thermometry or in their inability to reach optimal temperature for the tumor sites when noninvasive techniques are used, especially in the treatment of deep-seated tumors.

Localized heating utilizing a ferromagnetic alloy as "thermoseeds" has been investigated. These particles will generate heat when subjected to an applied alternating magnetic field (Jordan, et al., $2nd Int. Conf. Scientific and Clinical Applications of Magnetic Carriers$, Cleveland-Ohio, 29 (1998)). However, at least two impediments to clinical implementation have been identified: (1) the lack of uniform heat distribution at the tumor site and the resultant creation of spot overheating that leads to necrosis; and (2) the size of these thermoseed particles are on the order of 1 to 5 cm, making them highly non-biocompatible.

The ability to produce magnetic nanoparticles in recent years has enhanced interest in localized heating. In this technique, magnetic particles are confined on site and are heated by an external oscillating electromagnetic field (Lilly et al., $Radiology$, 154:243 (1985); Chan, et al., $J. Magn. Mater.$ 122:374 (1993); Jordan, et al., $Int. J. Hyperthermia$, 12:705 (1996)). Other examples are disclosed in Pankhurst et al., $Phys. D: Appl. Phys.$, 36:R167-81 (2003); Kuznetsov et al., $Eur. Cells Mater.$, 3:75-77 (2003); Jordan et al., $J. Magn.$ $Magn. Mater.$, 201:413-19 (1999). The use of nanomagnetic particles to induce heat at the tumor tissue potentially would minimize side effects by localized heating of only the desired parts of the organism, including tumors located deep inside a patient's body. Unfortunately, conventional magnetic particles make it impossible to control the uneven heating at the tumor site, which may cause local overheating and necrosis of healthy tissue.

It therefore would be desirable to provide improved magnetic particle compositions that reduce or eliminate the problem of uneven heating, and possess a property to self regulate the maximum temperature it can attain making magnetic hyperthermia a more viable therapeutic option.

SUMMARY OF THE INVENTION

Magnetic nanoparticle compositions are provided which provide an inherent temperature regulator for use in magnetic heating, particularly for use in magnetic hyperthermia medical treatments. In one aspect, a composition is provided that includes magnetic nanoparticles having a Curie temperature of between 40 and 46° C., for example, between 41 and 44° C., preferably about 42° C.

In one embodiment, the magnetic nanoparticles comprise an alloy of copper and nickel. For example, the alloy can be 71 to 71.4 wt % nickel, e.g., where the alloy is 71 wt % nickel and 29 wt % copper.

In another embodiment, the nanoparticles comprise a ferrite. For example, the ferrite can be selected from Zn ferrite, Gd-substituted Zn ferrite, Mn—Zn ferrite, Gd-substituted Mn—Zn-ferrite, and Fe—Zn ferrite. In one particular embodiment, the nanoparticles have a composition of the formula $Mn_{0.5}Zn_{0.5}Gd_xFe_{(2-x)}O_4$, where x is between 0 and 1.5. In another particular embodiment, the nanoparticles have a composition of the formula $Zn_xMn_{(1-x)}Fe_2O_4$, where x is between 0.6 and 0.8. In still another particular embodiment, the nanoparticles have a composition of the formula $Fe_{(1-x)}Zn_xFe_2O_4$, where x is between 0.7 and 0.9. In yet another particular embodiment, the nanoparticles have a composition of the formula $ZnGd_xFe_{(2-x)}O_4$, where x is between 0.01 and 0.8.

In various embodiments, the magnetic nanoparticles have an effective mean diameter of between 5 nm and 400 nm.

In several embodiments, the composition further includes a polymeric material. For example, the nanoparticles may be coated by or dispersed in a biocompatible polymeric material.

In another embodiment, the composition further includes at least one drug. In one particular embodiment, the magnetic nanoparticles and the drug are contained (e.g., encapsulated) in a biodegradable polymeric material, which may be in the form of microparticles or nanoparticles.

The nanoparticles of the composition can be made by various techniques. In one embodiment, the nanoparticles are made by a process comprising the steps of: (a) forming a melt which comprises at least two different metals; (b) solidifying the melt to form a bulk solid alloy of the metals; (c) grinding the bulk solid alloy to form particles of the alloy; and (d) subjecting the particles to a ball milling process effective to form magnetic nanoparticles of the alloy. For example, the at least two elemental metals may include copper and nickel. In another embodiment, the magnetic nanoparticles are made by a chemical coprecipitation process.

In another aspect, methods are provided for hyperthermia treatment of a patient in need thereof. In one embodiment, the method includes administering to the patient a composition comprising magnetic nanoparticles having a Curie temperature of between 40 and 46° C.; and then exposing the magnetic nanoparticles in the patient to an alternating magnetic field effective to generate hysteresis heat in the nanoparticles. In a preferred embodiment, the composition is administered to a tumor or other diseased tissue in the patient. The nanoparticles may be coated by a biocompatible polymeric material. In another embodiment, the magnetic nanoparticles are administered to a cancerous tissue site and the cancerous tissue site is further treated with one or more therapeutic drugs, one or more therapeutic radiation treatments, or a combination thereof.

In another aspect, a pharmaceutical composition is provided that includes magnetic nanoparticles having a Curie temperature of between 41 and 44° C., and a pharmaceutically acceptable carrier.

DESCRIPTION OF THE INVENTION

Figure 1:
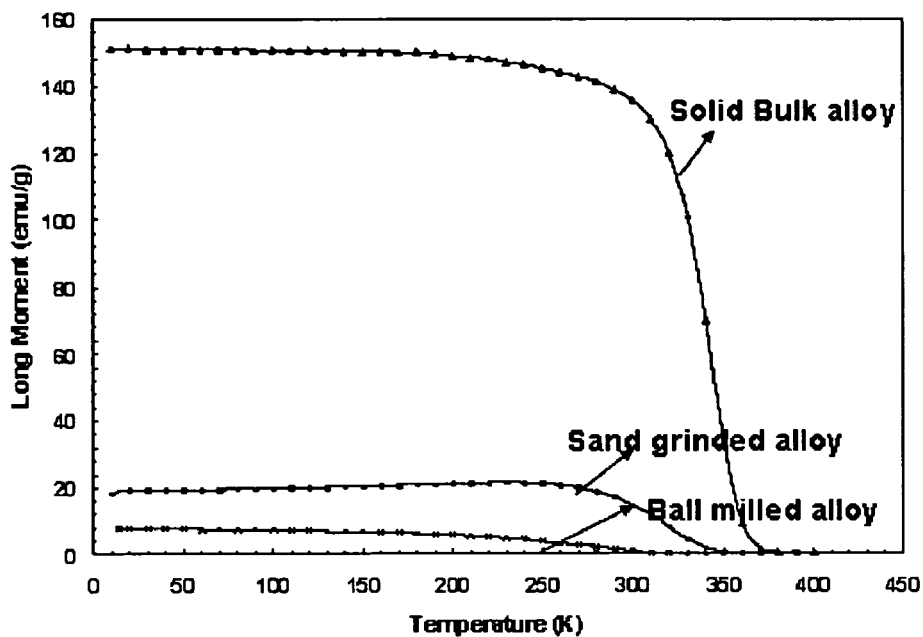
FIG. 1 is a graph showing the magnetization and magnetic phase transition (Curie temperature) for a copper/nickel alloy in bulk, ground powder, and ball milled nanoparticulate forms, in a magnetic field of 100 Oe, illustrating the change in magnetic characteristics that occurs as the alloy is processed into nanoparticle form.

Magnetic materials, such as particles, more particularly nanoparticles, have been developed that have specific and narrow Curie temperatures (Tc), which allows the materials to be magnetically heated to a predetermined, limiting temperature, thereby enhancing their desirability in therapeutic hyperthermia or other applications. One advantage of the magnetic material is that the treatment or therapy can be applied safely on patients without fear of overheating. Another advantage of this material is that by controlling the temperature at the limiting temperature, the effectiveness of a radio-sensitizing agent or drug may be significantly enhanced. In a preferred embodiment, the self-controlling magnetic material is used for magnetic hyperthermia, alone or in conjunction with targeted drug delivery, diagnostic imaging, or both drug delivery and imaging For instance, the magnetic particles described herein can be used as a contrast agent for magnetic resonance imaging (MRI) and as a self-controlled heating element at a tissue (e.g., tumor) site.

In a preferred embodiment, the magnetic material is in the form of nanoparticles, provided in a biocompatible form, wherein the magnetic nanoparticles have a Curie temperature in the range of 40 to 46° C., more preferably between 41 to 43° C., which is desirable to provide a safeguard against overheating of normal cells, due to the decrease of magnetic coupling in the paramagnetic regime above Tc. In one embodiment for hyperthermia treatment of a tumor, the magnetic particles are administered at the tumor site, an external alternating current (AC) magnetic field is applied to heat the particles, and the heat is conducted to the tumor cells.

As used herein, the terms "comprise," "comprising," "include," and "including" are intended to be open, non-limiting terms, unless the contrary is expressly indicated.

The Composition

In one embodiment, a composition is provided which includes magnetic nanoparticles having a Curie temperature of between 40 and 46° C., for example between 41 and 45° C., between 42 and 44° C., or between 42 and 43° C. In a preferred sub-embodiment, the magnetic nanoparticles have a Curie temperature of about 42° C. The composition preferably is biocompatible, so that it is suitable for administration to human and animal patients. Preferably, the nanoparticles have a high saturation magnetization and pyromagnetic coefficient (i.e., high $(\partial M/\partial T)_H$) so that a small change in magnetic field can cause a larger change in the temperature.

The magnetic nanoparticles preferably have an effective mean diameter of between 3 nm and 400 nm, although it certain applications it may be suitable or desirable to have larger nanoparticles. In one embodiment, the nanoparticles have an average diameter greater than about 5 nm (e.g., 10 nm, 20 nm, 40 nm, 50 nm, etc.) and less than about 350 nm (e.g., 325 nm, 300 nm, 275 nm, 250 nm, 200 nm, etc.).

As used herein, the term "magnetic nanoparticles" includes magnetic, paramagnetic, superparamagnetic ferromagnetic and ferrimagnetic materials. The magnetic nanoparticles can have any essentially composition that has the selected Curie temperature and that can be effectively heated by application of a magnetic field. The nanoparticles may comprise iron, nickel, cobalt, gadolinium, manganese and/or their alloys. In one embodiment, the magnetic nanoparticles of the composition comprise an alloy of copper and nickel. In a particular embodiment, the alloy is 71 to 71.4 wt % nickel, with the balance consisting essentially of copper. In a preferred embodiment, the alloy is 71 wt % nickel and 29 wt % copper. In another embodiment, the magnetic nanoparticles comprise a Mn—Zn Ferrite, having the formula: $Zn_xMn_{(1-x)}Fe_2O_4$ where x is between 0.6 and 0.8. In one particular embodiment, the magnetic nanoparticles comprise a Gd-substituted Mn—Zn-Ferrite. In a particular embodiment, the ferrite has the composition $Mn_{0.5}Zn_{0.5}Gd_xFe_{(2-x)}O_4$, where x is between 0 and 1.5. In another embodiment, the iron has a composition of $Fe_{(1-x)}Zn_xFe_2O_4$ where x is between 0.7 and 0.9. In another embodiment, the combination is in the form of $ZnFe_2O_4$. In another embodiment, the combination is in the form of $ZnGd_xFe_{(2-x)}O_4$, where x between 0.01 and 0.8.

The magnetic nanoparticles preferably are administered in a pharmaceutically acceptable carrier. In one embodiment, the magnetic particles with the selected Curie temperature are mixed into a liquid suspension or are encapsulated into microcapsules, which may then be mixed with a suitable biocompatible medium. For example, the magnetic particles can be bound in a matrix material to form a microcapsule. Important properties of microcapsules are their density and their diameter. The density affects the efficiency of their carriage by the blood stream to the site of immobilization in the diseased tissues vascular network while the size determines the proximity of the point of immobilization to the diseased tissue. In one embodiment, biocompatible coatings may be used to minimize the metallic interaction of the alloy particles with biological compounds, if necessary to enhance biocompatibility of the magnetic particles.

In one embodiment, the composition includes a polymeric material. For example, the magnetic nanoparticles can be dispersed in or encapsulated by a biocompatible polymer. The term "polymeric" is understood to mean that the composition comprises one or more oligomers, polymers, copolymers, or blends thereof. In one embodiment, the matrix material comprises a thermoplastic polymer. Examples of polymers include polyvinyl alcohol, poly ethylene glycol, ethyl cellulose, polyolefins, polyesters, nonpeptide polyamines, polyamides, polycarbonates, polyalkenes, polyvinyl ethers, polyglycolides, cellulose ethers, polyvinyl halides, polyhydroxyalkanoates, polyanhydrides, polystyrenes, polyacrylates, polymethacrylates, polyurethanes, andcopolymers and blends thereof.

For use in vivo, the polymeric material is biocompatible, and preferably biodegradable. Examples of suitable polymers include ethylcelluloses, polystyrenes, poly(ε-caprolactone), poly(d,1-lactic acid) and poly(d,1-lactic acid-co-glycolic acid). The polymer is preferably a copolymer of lactic acid and glycolic acid (e.g., PLGA).

In one embodiment, the magnetic nanoparticles and a drug are encapsulated in a thermosensitive material. In a preferred sub-embodiment, the melting temperature of the thermosensitive encapsulant material is equal to or slightly less than the nanomagnetic particle's Curie temperature. When these magnetic nanoparticles are heated, the heat generated melts the thermosensitive encapsulant, thus releasing the carried drug, at, for example, the site of tumor or treatment, and heats the tumor to further facilitate the treatment at the tumor site.

In various embodiments, the magnetic nanoparticles are encapsulated as described in U.S. Application Publication No. 2004/0065969 to Chatterjee, et al. and U.S. Application Publication No. 2004/0146529 to Chen, et al. The disclosures of these publications are expressly incorporated by reference herein.

In a further embodiment, the composition further includes a drug or radiosensitizing agent, as known in the art. In a preferred embodiment, the drug is a chemotherapeutic agent. Representative examples of chemotherapeutic agents known in the art include platins, such as carboplatin and cisplatin, taxanes, such as docetaxel and paclitaxel, gemcitabine, VP16, mitomycin, idoxuridine, topoisomerase 1 inhibitors, such as irinotecan, topotecan and camptothecins, nitrosoureas, such as BCNU, ACNU or MCNU, methotrexate, bleomycin, adriamycin, cytoxan and vincristine, immunomodulating cytokines, such as IL2, IL6, IL12 and IL13, and interferons. Certain chemotherapeutic agents are known to be potentiated by heating the tissue and/or the chemotherapeutic agent. Examples of possible heat-activated or heat-enhanced chemotherapeutic agents include bleomycin, BCNU, cisplatin, cyclophosphamide, melphalan, mitoxantrone, mitomycin C, thiotepa, misonidazole, 5-thi-D-glucose, amphotericin B, cysteine, cysteamine and AET. Representative examples of radiosensitizing agent include misonidazole, pimonidazole, 5-fluorouracil, and 2,4-dinitroimidazole-1-ethanol. Those skilled in the art can select the appropriate agent(s) for the particular patient, cancer or indication.

In one embodiment, the composition includes a suitable pharmaceutically acceptable carrier. For example, the carrier may be a pharmaceutically acceptable vehicles for injection. The pharmaceutically acceptable vehicle can be any aqueous or non-aqueous vehicle known in the art. Examples of aqueous vehicles include physiological saline solutions, solutions of sugars such as dextrose or mannitol, and pharmaceutically acceptable buffered solutions, and examples of non-aqueous vehicles include fixed vegetable oils, glycerin, polyethylene glycols, alcohols, and ethyl oleate. The vehicle may further include antibacterial preservatives, antioxidants, tonicity agents, buffers, stabilizers, or other components.

Methods of Making the Magnetic Nanoparticles

The magnetic nanoparticles can be made by essentially any process that yields the appropriate Curie temperature for the materials of construction. In one technique, the nanoparticles are made by a mechanical/physical size reduction process. In another technique a co-precipitation process is used to make the magnetic nanoparticles.

Preferably, the production process optimizes characteristics (besides Curie temperature) of the nanoparticles (e.g., crystallinity, grain size) that influences the nanoparticles effectiveness for use in magnetic hyperthermia. For instance, the nanoparticles desirably have a high pyromagnetic coefficient. Bimetallic nanoparticles can be synthesized by a wide variety of physical methods, such as, sputtering, mechanical alloying (ball milling), eletrodeposition or partial recrystallization of amorphous materials. Most of the methods yield two-phase nanocrystalline materials. Control of the composition in the nanolevel is typically difficult, since molecules and atoms in common techniques (e.g., chemical vapor deposition, plasma vapor deposition) do not necessarily arrange in the preferred composition, which was determined on bulk material on the macroscopic level.

In a preferred embodiment, the nanoparticles are made by a process comprising the steps of: (a) forming a melt which comprises at least two different metals; solidifying the melt to form a bulk solid alloy of the metals; (b) grinding the bulk solid alloy to form particles of the alloy; and (c) milling the particles into magnetic nanoparticles of the alloy. In a preferred embodiment, the milling step is carried out by a ball milling process. In a preferred embodiment, the two different metals are copper and nickel. In one embodiment, the melt is formed by mixing a measured quantity of a first metal in powder form with a measured quantity of a second metal in powder form. This mixing step, as well as the grinding and milling steps may be performed in an inert liquid. One embodiment of this process is described in Example 1 below, wherein copper-nickel alloy particles in the sub-micron range were made.

In yet another embodiment, Mn—Zn Ferrite nanoparticles are made by physical means. For example, in one process, Mn(II), Zn(II) and Fe(III) oxides or carbonates are sintered at high temperatures (up to 1200° C.), followed by high-energy ball milling and other means to reduce the particle size.

In another embodiment, a binary alloy is prepared by an arc melting technique. For example, nickel-chromium alloys with different compositions of Ni and Cr can be prepared using arc melting under argon gas atmosphere. To insure homogeneity, the composition can be re-melted. The material then can be annealed, for example, under argon gas atmosphere. The material can be then balled milled to reduce the size to a suitable nanoparticle size.

In another embodiment, the nanoparticles are synthesized by a chemical process. The primary advantage that chemical processes offer over other methods is good chemical homogeneity, as chemical synthesis offers mixing at molecular level.

In a preferred embodiment, a chemical co-precipitation method is used to make the magnetic nanoparticles. For example, chemical co-precipitation can be used to synthesize ferrite ($Fe_3O_4$) nanoparticles, as well as many other ferrites, such as Zn ferrite, Mn—Zn ferrite, and Cu ferrite. Ferrite fine particles are obtained by the co-precipitation from aqueous solutions of trivalent $Fe^{3+}$ and bivalent metal $Me^{2+}$, where $Fe^{2+}$, $Mn^{2+}$, $Co^{2+}$, $Ni^{2+}$ and/or $Zn^{2+}$ may serve as $Me^{2+}$. The initial molar proportion ($Me^{2+}/Fe^{3+}$) is always taken as the stoichiometric ½. The co-precipitation reaction generally takes place in two steps: a co-precipitation step and a ferritisation step. In the first step, solid hydroxides of metals in the form of colloidal particles are obtained by the co-precipitation of metal cations in alkaline medium. For the case of Mn—Zn ferrite, this reaction is as follows:

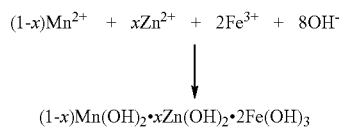

In the second step, the product of the first step is subjected to heating in a precipitation alkaline solution to provide the transformation of solid solution of metal hydroxides to the ferrite. For the case of Mn—Zn ferrite, this can be illustrated as follows:

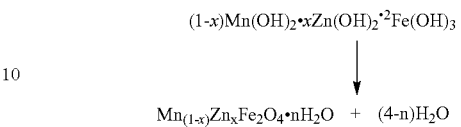

A particular feature of "the co-precipitation method" is that the product contains a certain amount of associated water even after several hours of heating in alkaline solution.

The rate of mixing of reagents plays a vital role in the size of the resultant particles. Co-precipitation consists of two processes: nucleation (formation of centers of crystallization) and a subsequent growth of particles. The relative rates of these two processes determine the size and polydispersity of obtained particles. Polydispersed colloids are obtained as a result of simultaneous formation of new nuclei and growth of the earlier formed particles. Less dispersed in size colloid is formed when the rate of nucleation is high and the rate of particles growth is low. This situation corresponds to a rapid addition and a vigorous mixing of reagents in the reaction.

Slow addition of reagents in the coprecipitation reaction leads to the formation of bigger nuclei than rapid addition. It must be also taken into account that in the case of slow addition of the base to solution of metal salts, a separate precipitation takes place due to the different pH of precipitation $pH_{pr}$ for different metals. Separate precipitation may increase the chemical inhomogeneity in the particles. To obtain ferrite particles of a smaller size, less dispersed in size and more chemically homogeneous the mixing of reagents must be performed as fast as possible.

An increase in temperature (in the range 20-100° C.) significantly accelerates formation of ferrite particles. The activation energy for formation of ferrites of different metals is not equal. The heating at temperatures close to 100° C. is preferable for an easier and more rapid formation of the Mn—Zn ferrite particles.

Non-limiting, exemplary embodiments of co-precipitation processes are described below in Example 5 and in Example 3, wherein $Mn_{0.5}Zn_{0.5}Gd_xFe_{(2-x)}O_4$ nanoparticles having a low Curie temperature and a moderately high value of magnetization and a high pyromagnetic coefficient were made using a chemical coprecipitation method. The pyromagnetic co-efficient of a material can be enhanced by gadolinium substitution.

In one embodiment for making nanoparticles, liquid polyols such as ethylene glycol or diethylene are used both as a solvent and as a reducing agent for the chemical preparation of metallic powders from various inorganic precursors. The basic reaction scheme for the synthesis of these metal powders by the polyol process involves: (a) dissolution of the solid precursor; (b) reduction of the dissolved metallic species by the polyol itself, (c) nucleation of the metallic phase; and (d) growth of the nuclei. To obtain metallic powders with a narrow size distribution, it is desirable that two conditions be fulfilled: (1) a complete separation of the nucleation and growth steps; and (2) avoidance of aggregation of the metal particles during the nucleation and growth steps. The general procedure for the synthesis of different metallic powders and films involved suspending the corresponding metal precursors in ethylene glycol or tetraethylene glycol and subsequently bringing the resulting mixture to refluxing temperature (generally between 120 to 200° C.) for one to three hours. During this reaction time, the metallic moieties are precipitated out of the mixture. The metal-glycol mixture is then cooled to room temperature, filtered, and the collected precipitate is dried in air. For film deposition, substrates are immersed in the reaction mixture. Compared to aqueous methods, the polyol approach results in synthesis of metallic nanoparticles protected by surface adsorbed glycol, thus minimizing unwanted oxidation.

Methods of Using the Composition

Generally, the method includes placing the magnetic material having a selected Curie temperature (or selected Curie temperature range) at a site intended for heating, and then exposing the magnetic material to an alternating magnetic field to generate hysteresis heat for a period of time effective for a particular result. While the site often would be in a patient for medical applications, the material optional could be used in industrial or other non-medical applications.

In one embodiment, a method of hyperthermia treatment of a patient in need thereof is provided which comprises: administering to the patient a composition comprising magnetic nanoparticles having a Curie temperature of between 40 and 46° C.; and exposing the magnetic nanoparticles in the patient to an alternating magnetic field effective to generate hysteresis heat in the nanoparticles. In a preferred embodiment, the heating method is used for site-specific treatment of diseased tissue in a patient. For example, the method can include the steps of: (i) providing a biocompatible composition comprising magnetic nanoparticles with Curie temperature of between 40 and 46° C., more preferably between 42 and 44° C; (ii) delivering the biocompatible composition to diseased tissue in a patient; and (iii) exposing the biocompatible composition in the patient to an alternating magnetic field to generate hysteresis heat in the diseased tissue, preferably until the diseased tissue has been destroyed or treated sufficiently to ameliorate the disease. The diseased tissue can, for example, be a tumor.

In an optional embodiment, the magnetic nanoparticles are administered to a cancerous tissue site in a patient and the cancerous tissue is further treated with one or more therapeutic drugs, one or more therapeutic radiation treatments, or a combination thereof. For instance, the method of treatment optionally can further include delivering to the diseased tissue radiation, a radiosensitizing agent, and/or a chemotherapeutic agent, as known in the art. The radiosensitizing or chemotherapeutic agent can be delivered as part of the magnetic particle composition or separately (simultaneously to, or before or after administration of the magnetic particles) from the magnetic nanoparticles.

In another embodiment, the method comprises the steps of: (i) providing a biocompatible composition comprising (a) magnetic nanoparticles with Curie temperature between 40 and 46° C., more preferably between 42 and 44° C., (b) a matrix material, and (c) a drug; (ii) delivering the biocompatible composition to a site in vivo in a patient; and (iii) exposing the biocompatible composition in the patient to an alternating magnetic field to generate hysteresis heat to facilitate release of the drug from the composition, and to aid in destroying diseased tissue, if any, present at the site.

In one embodiment, the microcapsules comprising the magnetic particles further comprise one or more drugs for release. In one embodiment, the drug is encapsulated in the same matrix material encapsulating the magnetic particles. In one method, release of the drug is essentially independent of the heating of the magnetic particles. In another method, release of drug is increased or facilitated by heating of the magnetic particles. The heating may operate to (1) increase the porosity of the matrix material, (2) increase the rate of molecular diffusion through the matrix material, (3) enhance the biodegradation or dissolution of matrix material, or (4) effect combinations of these mechanisms. For example, in one embodiment, the composition comprises magnetic nanoparticles that are coated by or dispersed in a biocompatible polymeric matrix material (e.g., in the form of larger micro- or nano-particles) that contains the drug, and magnetic heating expands the polymer to allow for the drug to diffuse out at the tumor site.

The compositions and methods also may be used in other hyperthermia treatments besides cancer treatment. For example, magnetic hyperthermia can be used in pain relief, controlling bleeding, or in the treatment of prostatic hypertrophy or psoriasis.

The biocompatible composition may be delivered to the diseased tissue in a patient by any means known in the art. Representative examples of suitable routes of administration include intratumoral, peritumoral and intravascular administrations (e.g., intra-arterial, intraperitoneal, subcutaneous, or intrathecal injection). In one embodiment, the biocompatible composition is delivered to the diseased tissue via the arterial or venous blood supply.

The magnetic field can be induced using simple magnets or other equipment well known in the art. The magnetic filed strength needed for effective alignment of the nanotubes can vary depending, for example, upon the amount of magnetic material attached to the nanotubes, the viscosity of the fluid medium, and the distance between the magnetic field and the fluid medium. The basic principle that allows this method to work is a balance between the magnetic force generated by the applied field (which is a function of the magnetic susceptibility, the volume of the magnetic material, the magnetic field, and the magnetic field gradient) and the resistance force (which is directly proportional to the viscous resistance of the fluid medium). In one embodiment, the strength of the magnetic field is between about 0.5 and about 1 T, inclusive of these end points.

The methods and compositions can be further understood with the following non-limiting examples.

EXAMPLE 1

Physically Synthesized Nickel-Copper Nanoparticles for Magnetic Hyperthermia

Nanoparticles, which consisted of a binary alloy of copper-nickel, having a preselected Curie temperature, were made.

The phase equilibria system for copper-nickel shows a linear progression for the Curie temperature, which starts at a composition of 67% nickel and 33% copper (by weight) for a temperature of 0° C. (Chakrabarti et al., *Binary alloy phase diagrams*, Materials Park, Ohio, 1990 Massalski et al. (editors)). From the Cu—Ni alloy phase diagram, the optimum amount of nickel in the alloy was selected to be 71-71.4% by weight, in order to yield an alloy having a Curie temperature in the range of 41 to 46° C.

The nanoparticles were made by process that combined melting and ball milling of bulk materials. The nickel-copper alloy was obtained via physical melting, in which nickel powder (AlfaAesar, 325 mesh, 99%) and copper powder (AlfaAesar, 500 mesh, 99%) were mixed in the desired composition (71% nickel, 29% copper; w/w). In order to obtain a highly homogenous composition over the resulting bulk alloy, the mixture was ball milled for 2 hours, before it was placed into an alumina crucible. The mixture was heated to 1465° C. for 3 hours, under nitrogen to prevent oxidation. (While the liquid temperature of the alloy is 1365° C., a higher temperature was used to avoid inaccuracies due to differences between actual and set temperature.) The liquid mixture was cooled to form a bulk chunk of the alloy. The resulting alloy was then processed in two steps to convert the bulk into particles of a desired size. First, a mechanical abrasion step was carried out to produce a powder texture that enables the second step, which includes the use of continuous grinding media. The first step included a simple and automated grinding process, and the second step included additional grinding in a ceramic ball mill for at least 3 to 7 days. The grinding was carried out in a wet environment using acetone in order to enhance the mixing of the materials being milled and to prevent oxidation of the materials and to prevent the formation of a toxic and uncollectible metallic particle gas. Ten ceramic (alumina) balls were used for 5 g of starting material. The ball weight to content weight ratio was 6. The rotation speed of a jar (40 mm in diameter) was 120 min$^{-1}$. After decanting from the jar, the dispersion was dried in vacuum. A highly dispersed gray is metallic suspension was obtained after the first day of ball milling.

A JEOL 2010 transmission electron microscope was used to determine the particle morphology. A ZetaPALS Particle Size Analyzer (Brookhaven Instrument Corp.) was used to determine the particle size. Magnetic properties were measured using an MPMS 5 Superconducting Quantum Interference Device (SQUID) magnetometer. Wide angle X-ray diffraction pattern was taken in a Siemens 500 X-ray diffractogram with CuKα ($\lambda$=0.154 nm) radiation.

FIG. 1 shows the magnetization of the as-produced bulk alloy, as well as the ground powder and ball-milled powder in a magnetic field of 100 Oe. It indicates for the as-produced powder a complete phase transition from ferromagnetic to paramagnetic behavior at 97° C. (370 K), which does not fall into our target temperature range. From FIG. 1, one can see a shift towards the target temperatures for the ground and ball-milled powders. The coarse sand-grinded powder (particle diameter <150 μm) shows a Curie temperature of about 72° C. (345 K) and the fine ball-milled powder (effective particle diameter: 436 nm) shows a temperature of about 46 to 47° C. (319 to 320 K).

Curie temperature also is related to the lattice constants. The Curie temperature increases with an increase in lattice constant (Gilleo, *Ferromagnetic Materials*, p. 34 (eds., E. P. Wohlfharth) (North Holland Physics Publishing 1986). Based on the electron diffraction (ED) pattern and the wide-angle X-ray diffraction pattern (XRD), the d-spacing value (between the 111 planes) was calculated and the result is shown in Table 1.

TABLE 1

Comparison of XRD on sand ground powder and Electron Diffraction on ball-milled powder

|     |                        | 2θ - angle (°) | d-spacing (Å) |
| --- | ---------------------- | -------------- | ------------- |
| XRD | (111) (1$^{st}$ peak)  | 44.24          | 2.045         |
| ED  | (111) Inner ring       | 44.44          | 2.036         |

Figure 2:
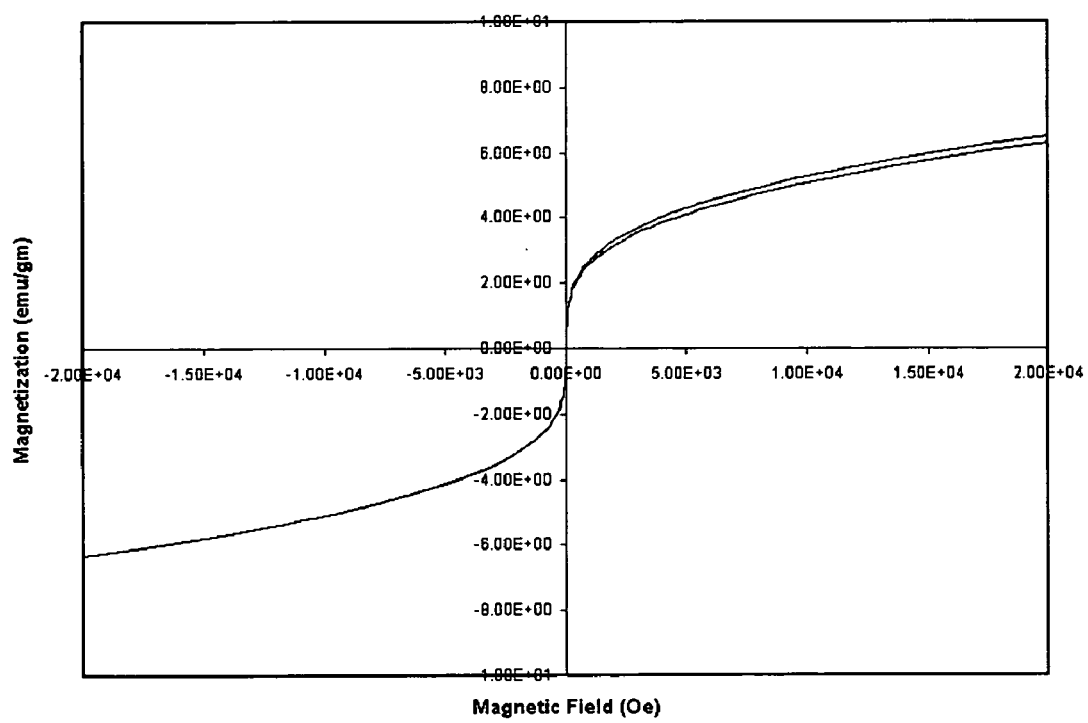
FIG. 2 shows a hysteresis plot of a ball milled nanoparticulate form of a copper/nickel alloy, exhibiting magnetic behavior similar to superparamagentic materials.

It was observed that the d-spacing changes from 2.045 in the sand-ground bulk alloy to 2.036 in the ball-milled Cu—Ni alloy particles. While not being bound to any theory, it is believed that this might be the reason for decrease in the Tc value observed in the ball-milled powder. That is, by ball milling, the nanostructure is obtained by repeated mechanical deformation using a number of milling balls, and the internal strain in the crystalline structure caused the change in the d-spacing. FIG. 2 shows the hysteresis plot of the ball-milled fine powder. There is no remanent magnetic moment at room temperature indicating the superparamagnetic behavior of the Cu—Ni ball milled powder.

Transmission electron microscopy (TEM) analysis and particle size analysis verified that sub-micron particles were obtained by the mechanical alloying method used. The particle size was measured after ultrasonication of an aqueous dispersion for a few minutes and resulted in an effective diameter of 436 nm with a half width distribution of 218 nm. The particles that were found during TEM analysis ranged from around 100 nm to a few micrometers. The population of spherical particles (~100 nm) was very low compared to particles with flake-like geometry. In these flake-like particles, submicron grains and boundaries also were observed along with little contrast. Since copper and nickel have almost the same density (Cu 8920 kg/m$^3$, Ni 8908 kg/m$^3$) and similar face-centered cubic lattices with nearly the same lattice constants, changes in contrasts are only due to different particle thicknesses. The texture of the particles reflects the abrasive nature of the ball milling process. Highly magnified (×200000) micrographs of the solid texture of a single (micron sized) particle showed clearly a polycrystalline structure with its grains and boundaries. The grains have submicron dimensions.

Nanomagnetic particles with desired Curie temperature were made, and the desired range of Curie temperatures was obtained by selection of the weight percentage of nickel and copper based on the phase diagram. Generating particles in submicron size appears to be important to vary the Curie temperature. Ball milling was found effective to generate submicron particles, and the combination of melting and ball milling was effective to produce alloy particles in large quantity, in what would appear to be a commercially viable process.

EXAMPLE 2

Synthesis of Nickel-Chromium ($Ni_{1-x}Cr_x$) Nanoparticles

A series of $Ni_{1-x}Cr_x$ alloys were prepared to find the specific composition that has a Curie temperature around 316-317 K. Magnetic properties of the samples were investigated, including Curie temperature, saturation magnetization and hysteresis. The Curie temperatures of the alloys were decreased from 401 K to 289 K, while increasing the Cr concentration from x=4.54 wt % to x=5.90 wt %. The results showed that ($Ni_{1-x}Cr_x$) alloys are good candidates for self regulating magnetic hyperthermia applications, because the Curie temperature of the alloys decreases almost linearly with increasing Cr concentration.

A series of NiCr binary alloys were prepared from nickel and chromium metals with 99.9% purity under a argon gas atmosphere by a standard arc melting technique. The samples were turned over and re-melted three times to ensure homogeneity. Finally the samples were annealed in argon gas filled and sealed quartz tubes at 850° C. for 5 hours.

Figure 3:
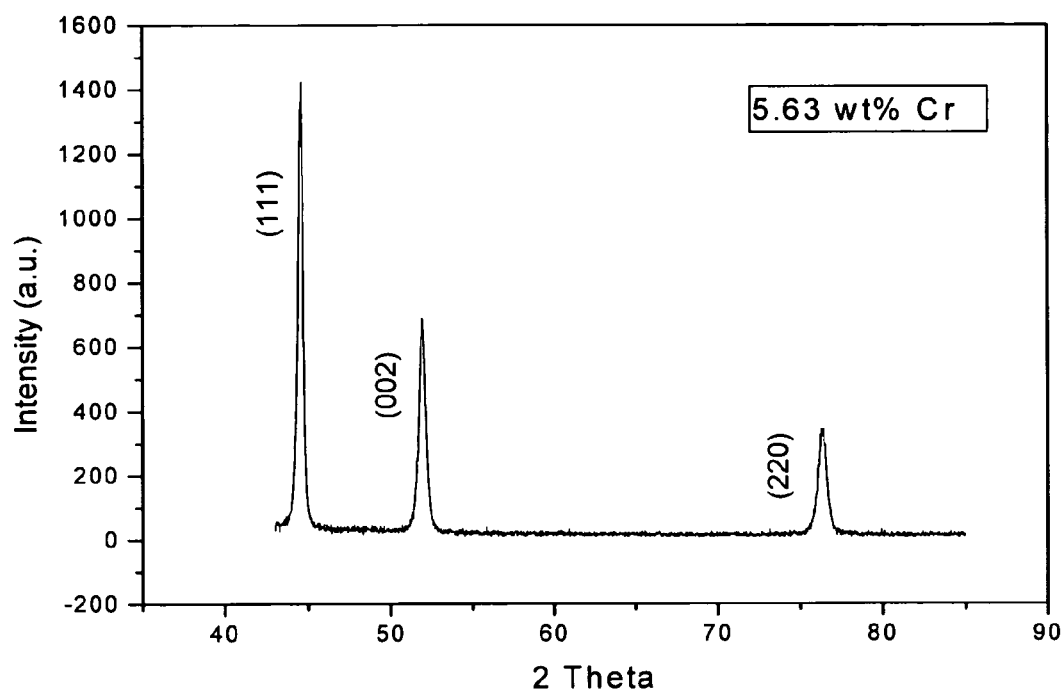
FIG. 3 is a graph illustrating XRD diffraction pattern of 94.37 wt % Ni and 5.63 wt % Cr.

Powder X-ray diffraction profiles were collected using a Siemens diffractometer with Cu Kα radiation. Data were collected at room temperature over the two ranges of 43° and 85° in 0.02° steps with an integration time of 2 seconds. Vibrating Sample Magnetometer (Lake Shore) and SQUID Magnetometer (Quantum Design) were used for magnetic characterization of the samples. The solubility of chromium in nickel is above 45% at the eutectic point, 1343° C. However, chromium-rich secondary β phase forms at lower temperatures when the chromium atomic percentage exceeds 30%. Magnetic transition temperature of the alloys also decreases with increasing atomic percentage of chromium in nickel. FIG. 3 shows an X-ray diffraction pattern obtained from a 5.63 wt % Cr and 94.37 wt % Ni sample which has 317 K Curie temperature. The XRD pattern is similar to the XRD pattern of pure Ni, and no extras or split peaks which correspond to the individual Cr or $Cr_2O_3$ phases are seen. This indicates that single phase solid solutions were obtained with the processing conditions over the range of chromium wt %.

Figure 4:
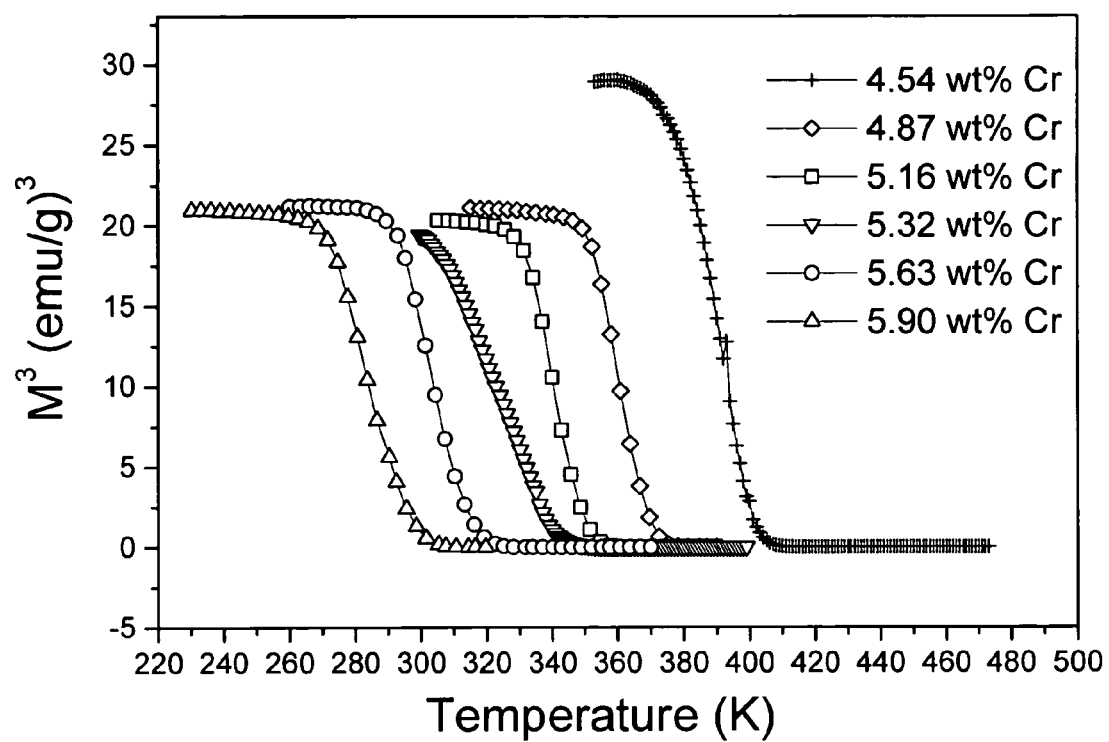
FIG. 4 is a graph illustrating the mass magnetization of $Ni_{1-x}Cr_x$ alloys versus temperature at H=100 Oe applied magnetic field parallel to the normal direction. The Curie temperatures of the samples were determined by $M^3$ versus T plots by extrapolating $M^3$ to zero.
Figure 5:
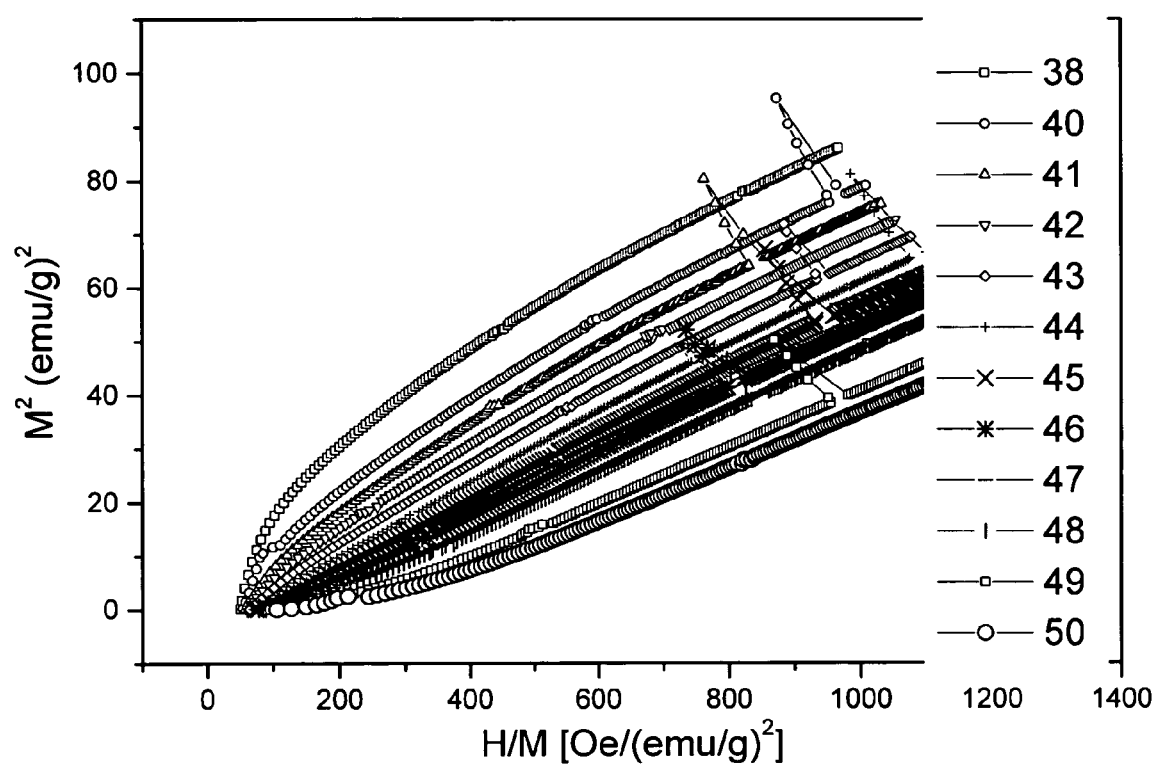
FIG. 5 is a graph illustrating Arrot's of Ni—5.63 wt % Cr.
Figure 6:
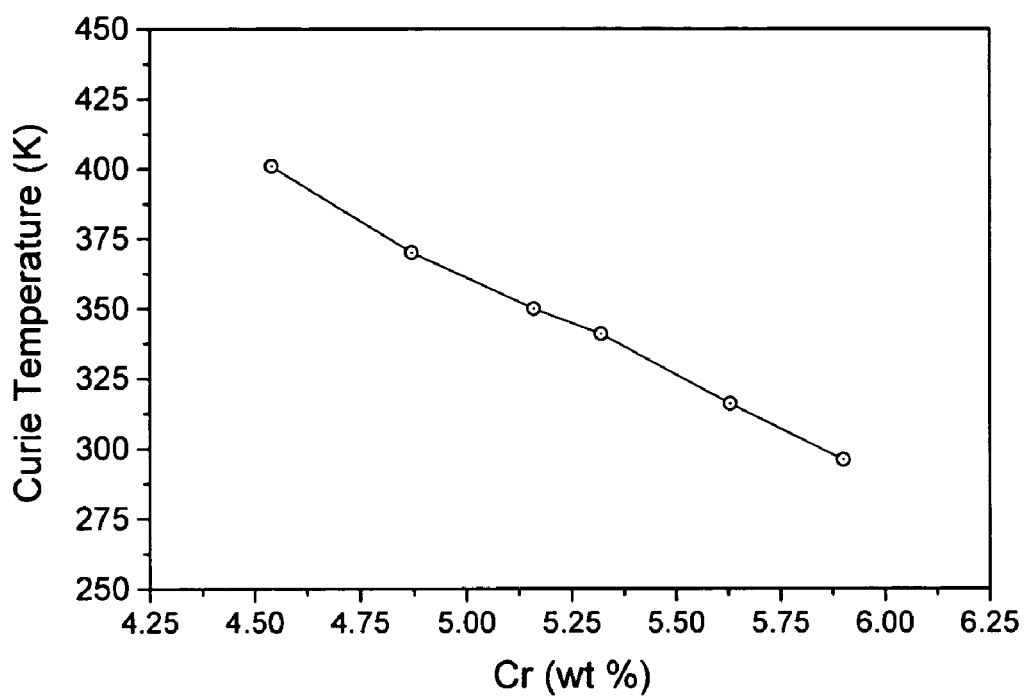
FIG. 6 is a graph illustrating the Curie temperature of $Ni_{1-x}Cr_x$ alloys versus Cr wt % concentration.

Magnetizations versus temperature experiments were conducted to measure the ordering temperature (Curie temperature (Tc)) of the samples. The Tc values of the samples were obtained using the relation of the spontaneous magnetization M α $(Tc-T)^\beta$ with β=⅓. The Curie temperatures of the samples were determined by $M^3$ versus T plots by extrapolating $M^3$ to zero and by the Arrot's plot. FIG. 4 shows the magnetization versus temperature of NiCr alloys in a magnetic field of 100 Oe. The samples showed sharp transition from ferromagnetic to paramagnetic properties while the temperature was increasing. FIG. 5 shows the Arrot's plots of Ni—5.63 wt % Cr. The Tc value of Ni—5.63 wt % Cr was obtained as 317 K from both graphs. The Tc values of the samples are also in good agreement with reported values. FIG. 6 shows Curie temperature versus Cr wt % concentration graph. Curie temperature of the samples decreased almost linearly with increasing Cr wt % concentration in nickel, which indicates that $Ni_{1-x}Cr_x$ alloys with desired Curie temperature can be processed by adjusting Cr concentration.

Figure 7:
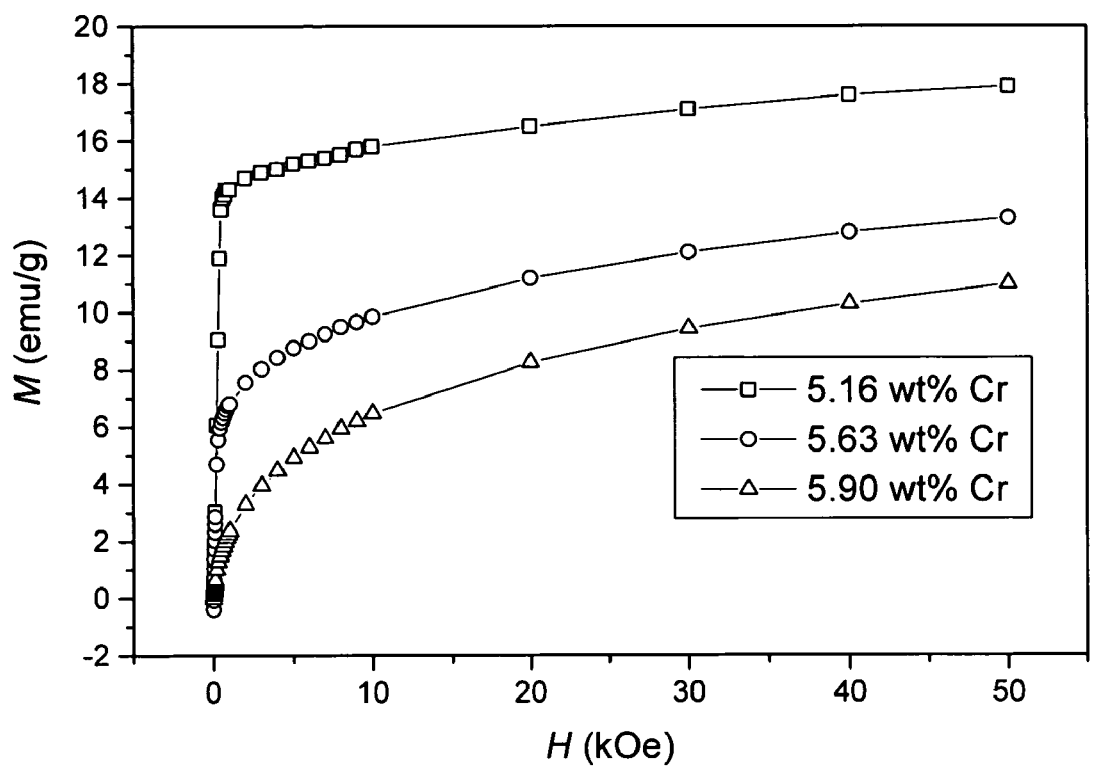
FIG. 7 is a graph illustrating the field dependence of the magnetization of $Ni_{1-x}Cr_x$ alloys at 300 K.

FIG. 7 shows field dependent mass magnetizations of $Ni_{1-x}Cr_x$ samples with 5.16, 5.63, and 5.90 wt % Cr. The measurements were conducted at 300 K. The maximum applied magnetic field was 50 kOe, in order to obtain the saturation magnetization. The samples were not saturated with applied 50 kOe at 300 K, as they are not purely in the ferromagnetic state at 300 K. Magnetizations (M) of the samples were increased with increasing applied magnetic field. Magnetization of the samples also decreased with increasing wt % Cr concentration in $Ni_{1-x}Cr_x$ alloys. The complete magnetization loops of the three samples show small hysteric losses.

EXAMPLE 3

Gadolinium Substitution on Mn—Zn-Ferrite Nanoparticles

Mn—Zn ferrite and Gd substituted Mn—Zn ferrite nanoparticles were synthesized using a chemical co-precipitation method to obtain low Curie temperature magnetic particles with a moderately high value of magnetization and a high pyromagnetic coefficient. The magnetic properties and temperature dependence of these particles, and the effect of varying Gd proportions, were studied. The particles exhibited properties that make would make them worth considering for hyperthermia applications.

Mn—Zn-ferrite particles and Gd substituted Mn—Zn-Ferrite particles were obtained via chemical co-precipitation and ferritization. First, the metal salts were co-precipitated into hydroxides. This was done by addition of aqueous solution of metal salts in water to the coprecipitating base (e.g. NaOH, $CH_3NH_3OH$ etc.). For the case of Mn—Zn Ferrite particles the reaction occurs as follows:

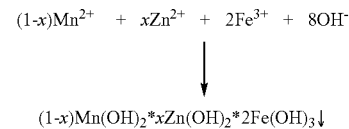

Then this precipitate is transformed into ferrite by heating in the precipitation alkaline solution (ferritization). The reaction for Mn—Zn ferrite particles is as follows:

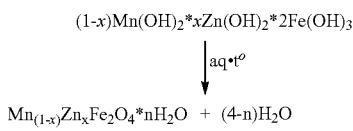

$FeCl_3 6H_2O$, $GdCl_3 6H_2O$, $MnCl_2 4H_2O$ and $ZnSO_4 7H_2O$ were used to obtain $Fe^{3+}$, $Gd^{3+}$, $Mn^{2+}$ and $Zn^{2+}$ ions in the aqueous solution. This salt solution at 90° C. was added to 8M NaOH solution at 90° C. followed by vigorous stirring. The stirring and heating at 90° C. was continued for a minimum of 40 minutes. The product was then filtered, washed with distilled water, and finally washed and dried with acetone. Six samples were made of $Mn_{0.5}Zn_{0.5}Gd_xFe_{(2-x)}O_4$, where x, the proportion of Gd, was equal to one of the following proportions 0, 0.2, 0.5, 0.7, 1.0, and 1.5. These samples were labeled S, T, U, V, W, and X, respectively.

All the samples were examined by X-ray powder diffraction (XRD). Hysteresis curves were obtained by using vibration sample magnetometer (VSM) by subjecting the samples to a field in the range of 0 to 5,000 G. A Quantum Design SQUID was used to study the temperature dependence of the magnetization, where a constant field of 100 G was applied to the sample and the moment was measured by varying the temperature from 0 K to 450 K.

Figure 8:
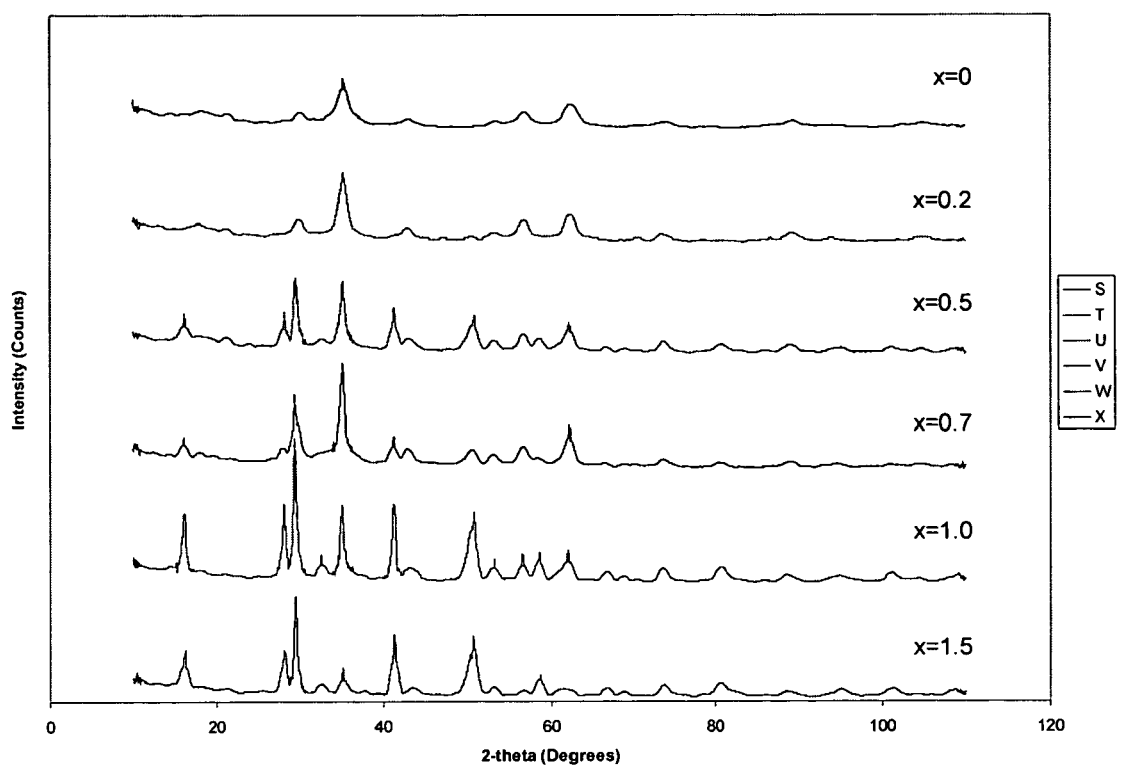
FIG. 8 is a graph illustrating X-ray powder diffraction results for samples of Mn—Zn-Ferrite nanoparticles and Gd-substituted Mn—Zn-Ferrite nanoparticles with different amounts of Gd in the composition.
Figure 9:
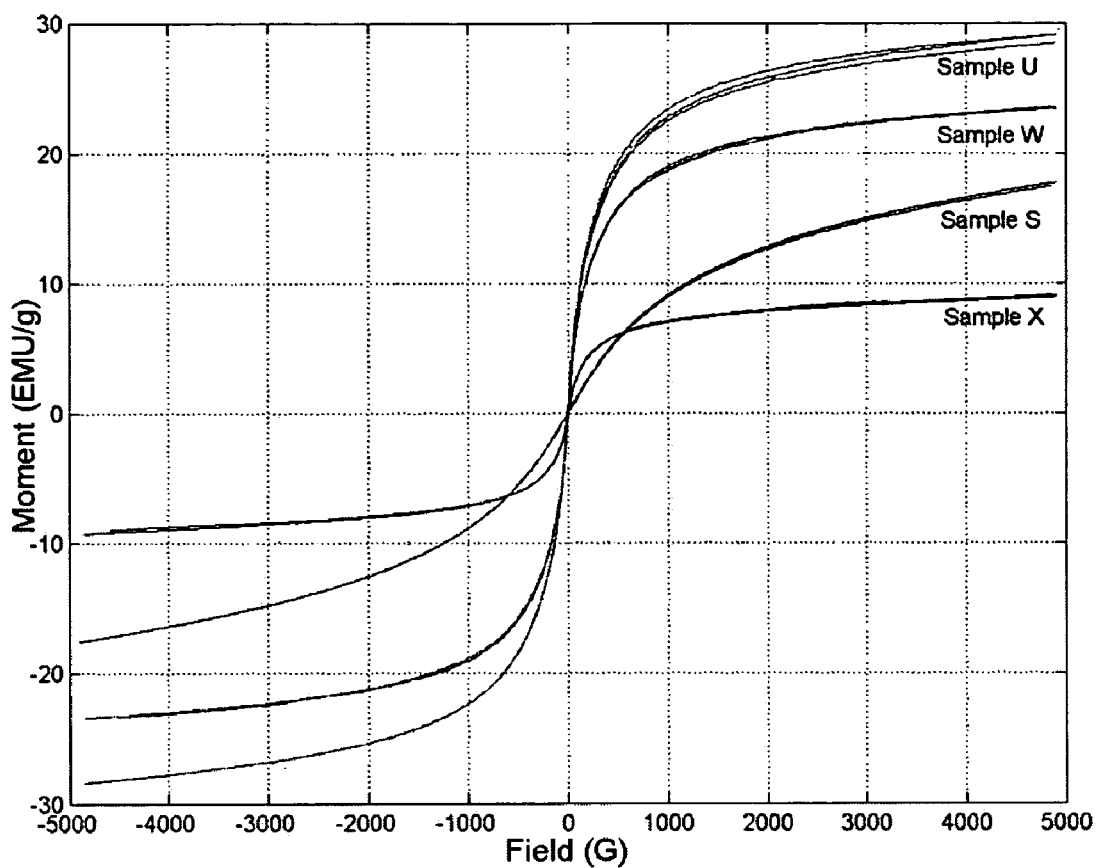
FIG. 9 is a plot of hystersis curves for various Gd-substituted Mn—Zn-Ferrite nanoparticles.

XRD diagrams for the samples are shown in FIG. 8, and demonstrate a spinel crystalline structure, which is typical for ferrites. The hysteresis curves for Samples S, U, W and X were observed to be soft-magnetic as shown in FIG. 9.

Figure 10:
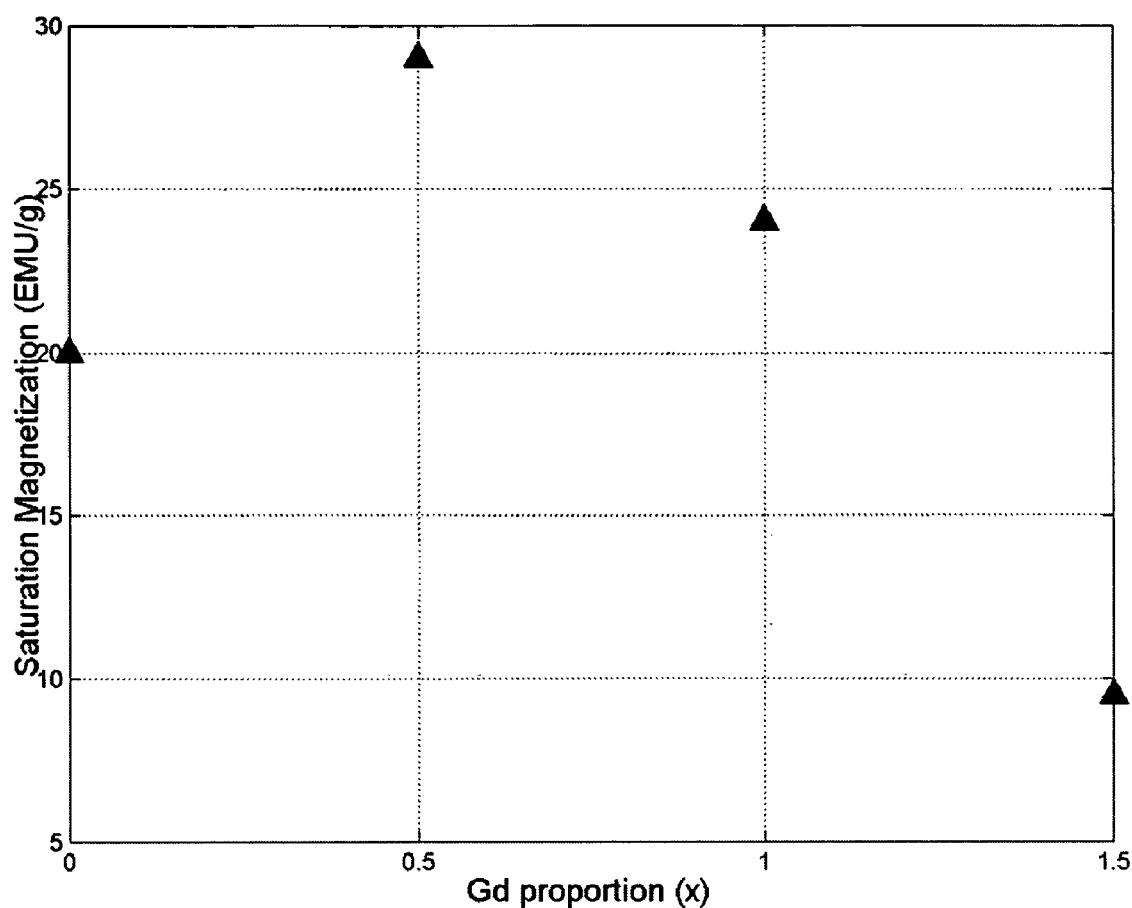
FIG. 10 is a graph illustrating the change in saturation magnetization with increasing Gd substitution for one embodiment of Gd-substituted Mn—Zn-Ferrite nanoparticles.

The variation in saturation magnetization with increasing Gd proportion is plotted in FIG. 10. It can be seen that the addition of gadolinium results in an increase in saturation magnetization, from 24 EMU/g for Sample S (x=0) to 29 EMU/g for Sample U (x=0.5). But addition of gadolinium beyond x=1.0 results in reduction of saturation magnetization the value being 24 EMU/g for Sample W (x=1.0) and 9.5 EMU/g for Sample X (x=1.5) (see Table 1). The initial increase in the saturation magnetization can be explained by considering that the $Gd^{3+}$ ions have a large spin only magnetic moment per atom (7 μB) as compared to that of $Fe^{3+}$ ion (5 μB). As a result, the net moment of the octahedral sites increases resulting in a corresponding increase in the saturation magnetization. Addition of $Gd^{3+}$ ions results in their occupancy of the octahedral sites, an occurrence attributable to their large ionic radii. Since the ionic radii of the $Gd^{3+}$ ions is large, there is a decrease in the distance between these and the oxygen ions when adding Gd ions consequently strengthening the B-B interaction (Smit & Wijn, *Ferrites*, John Wiley & Sons, NY, 1959, p 139-42). As a result the ions at the octahedral sites no longer have their moments parallel to each other. A part of these ions have moments aligned antiparallel to the other atoms on these octahedral sites. This results in a reduction in the net magnetic moment of the octahedral atoms. As the Gd substitution is increased, more and more octahedral atoms have their moments antiparallel. As a result, the saturation magnetization drops. In addition, Gd shows magnetic order at low temperatures. At room temperature, its magnetic moment is small—thus the decrease in the magnetization when increasing the Gd fraction.

Figure 11:
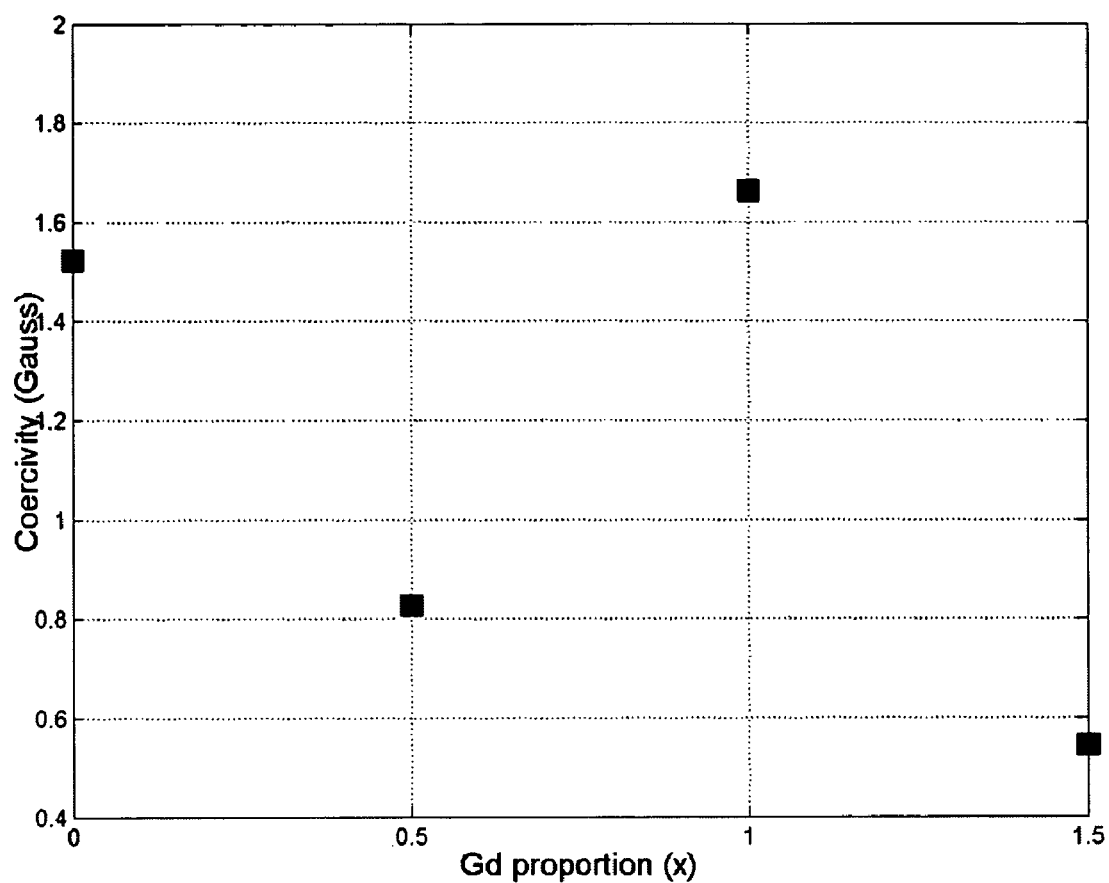
FIG. 11 is a graph illustrating the change in coercivity with increasing Gd substitution for one embodiment of Gd-substituted Mn—Zn-Ferrite nanoparticles.

The variation in coercivity with increasing Gd proportion is plotted in FIG. 11. The coercivity values show some fluctuations with an average value of 1.1 G.

Figure 12:
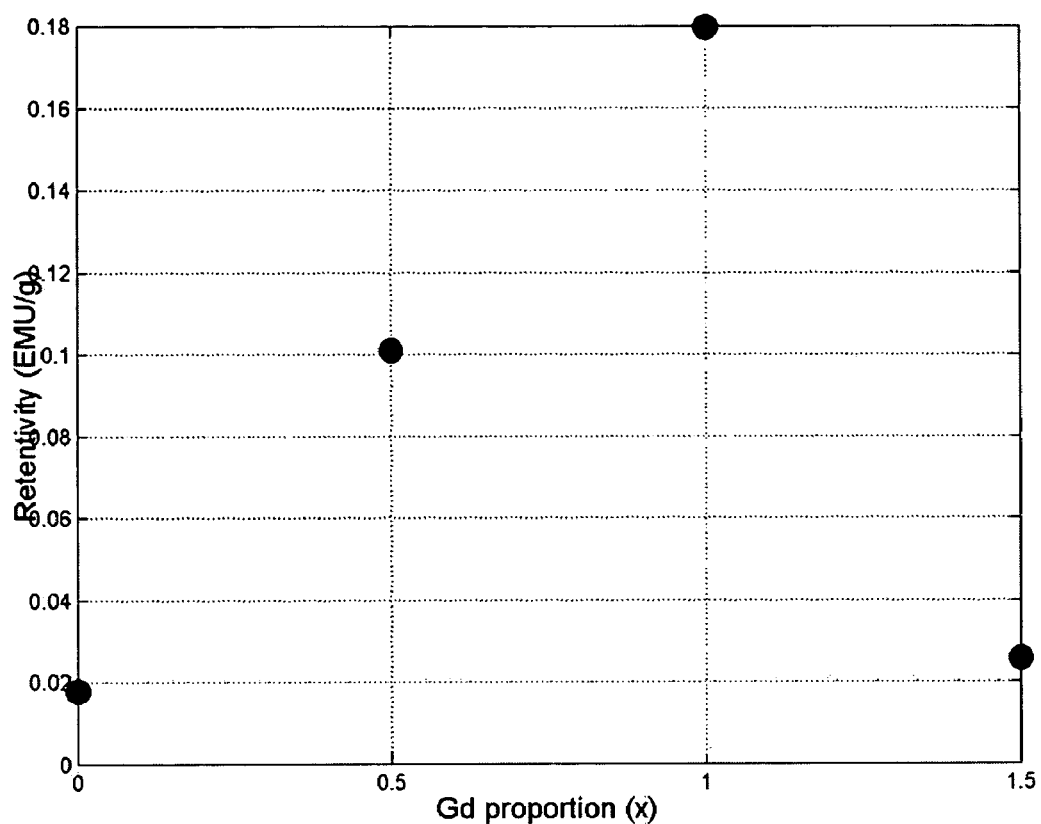
FIG. 12 is a graph illustrating the change in retentivity with increasing Gd substitution for one embodiment of Gd-substituted Mn—Zn-Ferrite nanoparticles.

Retentivity, which also is called Remanence, is the strength of the magnetic field that remains in the magnetic particles after it is exposed to a strong magnetic field and the external field is removed. The variation of retentivity with increasing Gd proportion is plotted in FIG. 12. There is a steady increase in retentivity up to x=1.0 (Sample W), yet further addition of Gd results in a drop in retentivity (Sample X: x=1.5).

Figure 13:
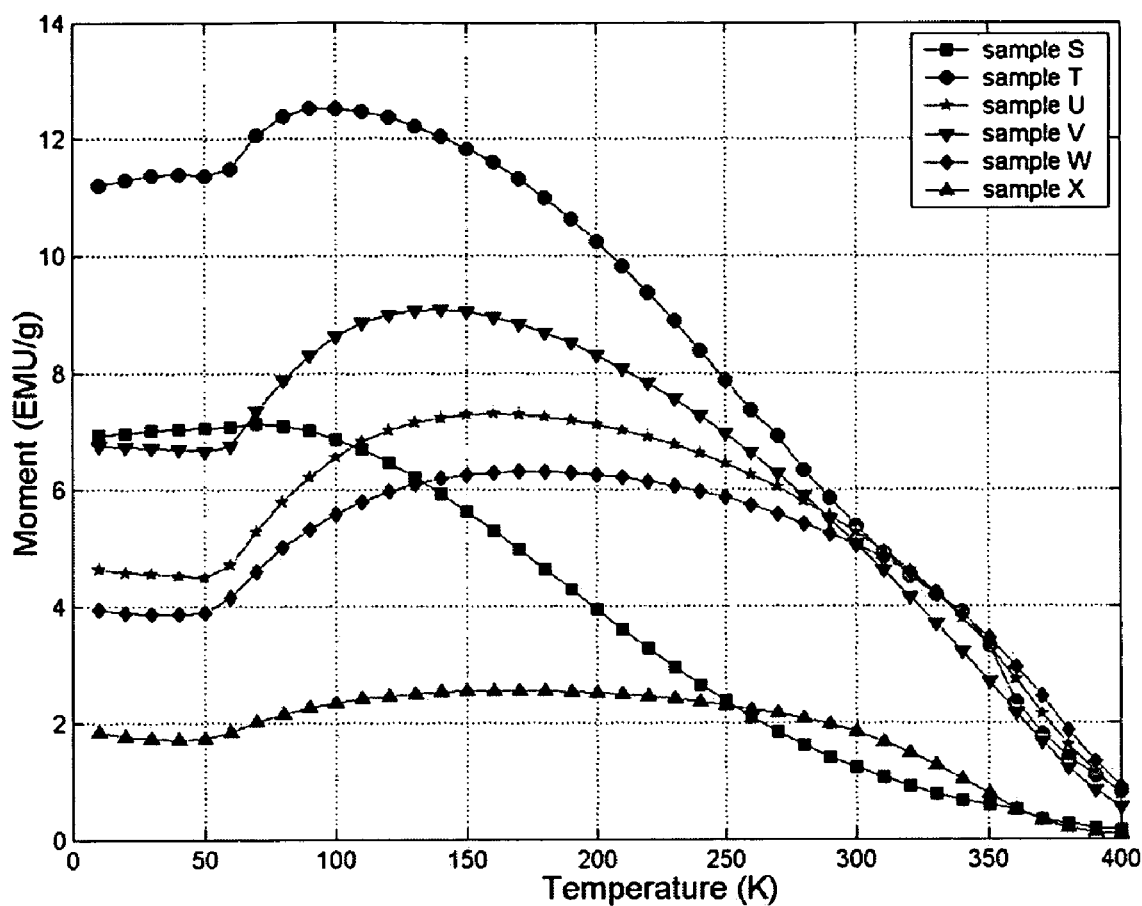
FIG. 13 is a graph illustrating the temperature dependence of magnetization for Mn—Zn-Ferrite nanoparticles and Gd-substituted Mn—Zn-Ferrite nanoparticles with different amounts of Gd in the composition.
Figure 14:
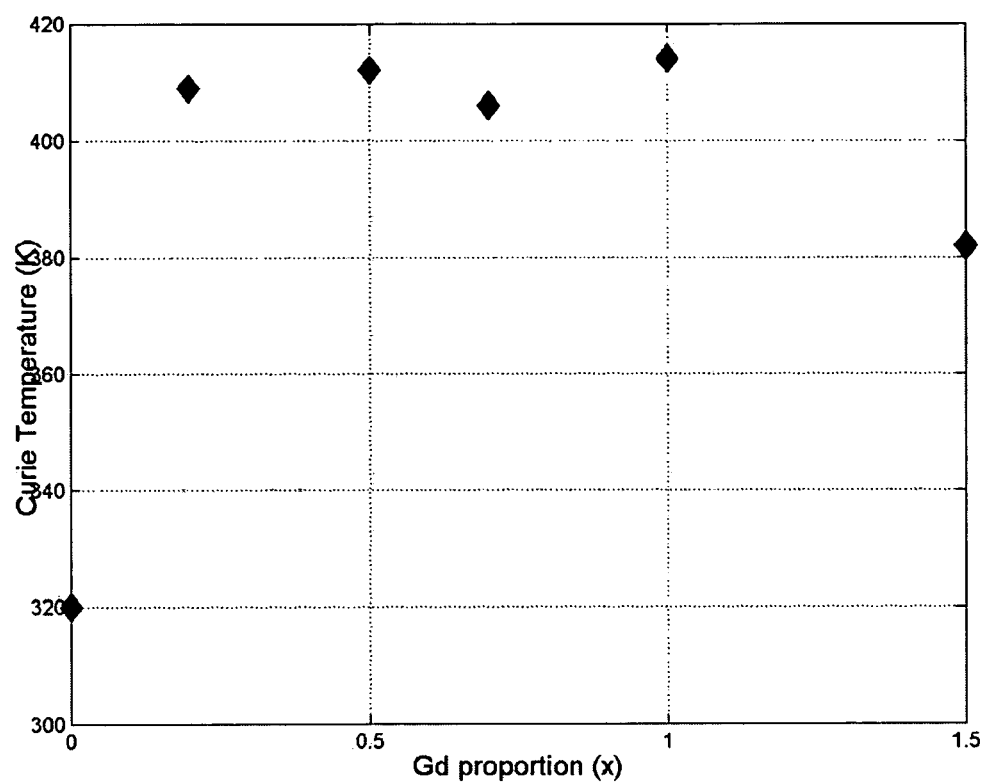
FIG. 14 is a graph illustrating the change in Curie temperature with increasing Gd substitution for one embodiment of Gd-substituted Mn—Zn-Ferrite nanoparticles.

FIG. 13 shows the superimposed temperature dependence plots for all the samples. The Curie temperature was calculated by extrapolation of the linear sections of the temperature dependence plots. The variation in Curie temperature with increasing Gd proportion is plotted in FIG. 14, where an increase in Curie temperature with Gd substitution can be observed. The Curie temperature increases from 320 K for Sample S (x=0) to about an average of 410 K for sample T (409 K), U (412 K), V (406 K) and W (414 K). Thus, the Curie temperature remains almost constant for x=0.2 until x=1.0. However, further addition of Gd results in a decrease in Curie temperature (Sample X: x=1.5: Tc=382 K). This variation in the Curie temperatures can be attributed to the changes in the B-B interaction due to addition of $Gd^{3+}$ ions.

The nanosize Mn—Zn ferrite and Gd substituted Mn—Zn ferrite particles were observed to be soft-magnetic. Addition of $Gd^{3+}$ ions up to proportions of x≦0.5 results in an increase in the net moment. Further addition of the $Gd^{3+}$ ions resulted in a decrease in the net moment. The saturation magnetization increases then decreased with increasing proportion of gadolinium. Coercivity did not show any clear trend, while the Retentivity increased until x=1.0 and decreased thereafter. The Curie temperature increased with addition of gadolinium, but addition of Gd beyond x=1.0 resulted in a decrease in Curie temperature.

TABLE 2

Magnetic Properties of the Samples

| Sample Name | Saturation Magnetization (EMU/g) | Coercivity (G) | Retentivity (EMU/g) | Curie Temperature (K.) |
|---|---|---|---|---|
| S | 20 | 1.5233 | 0.0179 | 320 |
| T | — | — | — | 409 |
| U | 29 | 0.8268 | 0.1011 | 412 |
| V | — | — | — | 406 |
| W | 24 | 1.6617 | 0.1796 | 414 |
| X | 9.5 | 0.5448 | 0.0256 | 382 |

EXAMPLE 4

Borohydride Reduction

Fe—Nd—B particles are usually synthesized using borohydride reduction, but have a very high Curie temperature of 310° C., well beyond the required optimum range of 42-43° C. So an attempt was made to replace Nd with Gd with an aim of lowering the Curie temperature. Fe—Gd—B nanoparticles were synthesized using borohydride reduction. Salts of the required metallic elements were reduced by sodium borohydride ($NaBH_4$). The procedure involved a dropwise addition of aqueous solution of metallic salts to $NaBH_4$ solution along with a vigorous stirring. The pH of the salt solution was maintained at 6, whereas that of the $NaBH_4$ was maintained at 12. NaOH can be added to the $NaBH_4$ solution to increase the pH to this level.

A 0.04 M solution of salts $GdCl_3$ and $FeSO_4$ mixed in the required stoichiometric proportions was added to a 1 M $NaBH_4$ solution kept in a round bottom flask. The resultant mixture was vigorously stirred. The reaction was carried out in an argon atmosphere by passing argon into the flask during the reaction. After complete addition of the salt solution, the reaction and stirring was allowed to continue for 40 minutes more. The reaction may be represented by the following chemical reaction:

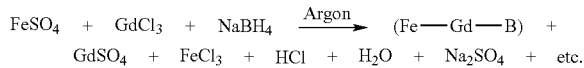

$$FeSO_4 + GdCl_3 + NaBH_4 \xrightarrow{Argon} (Fe-Gd-B) + GdSO_4 + FeCl_3 + HCl + H_2O + Na_2SO_4 + etc.$$

Three samples were made with Gd:Fe ratios of 80:20, 60:40 and 95:5.

EXAMPLE 5

Chemical Co-Precipitation

Chemical co-precipitation was used to make nanoparticles of Mn—Zn ferrite, Gd-substituted Mn—Zn ferrite, Fe—Zn ferrite, Zn ferrite, and Gd-substituted Zn ferrite. Salt solutions of the appropriate metallic elements were reduced by NaOH solution. The reactants when mixed were at temperatures of 90° C. After the mixing, the reaction was continued for 40 minutes along with heating at 90° C. The nanoparticles were synthesized with and compositions varied with the objective of making nanoparticles in the desired Curie temperature range of about 315° K. (42° C.). The results were as follows:

1. Mn—Zn ferrite nanoparticles with curie temperatures in the desired range were made by changing the Zn proportions.
2. Gd-substituted Mn—Zn ferrite nanoparticles with Mn:Zn ratio other than 1:1 were made.
3. Fe—Zn ferrite particles of the form $Zn_xFe_{1-x}Fe_2O_4$ with x=0.5 to x=0.7 were made, and Fe—Zn ferrite nanoparticles were synthesized with x>=0.7 with an aim of getting the Curie temperature down to the desired range of 315 K.
4. From the trend of Curie temperature of the Fe—Zn ferrite nanoparticles, it was observed that the Curie temperature of the nanoparticles decreased with increasing Zn proportions.
5. On comparing the characterization data of the Gd-substituted Mn—Zn ferrite particles with that of the Mn—Zn ferrite particles, it was noticed that addition of Gd in small amounts leads to an increase in the Curie temperature as well as the pyromagnetic co-efficient of the nanoparticles. Since the Curie temperature of the Zn ferrite was measured to be below the desired range, Gd-substituted Zn ferrite particles were synthesized to increase its Curie temperature.

EXAMPLE 6

Refluxing in Polyol Method

Ni—Cu nanoparticles were synthesized using the polyol process. The salts $NiCl_2$ and $CuSO_4$ were dissolved in ethylene glycol and refluxed at 195° C. for 11-12 hrs.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A composition comprising magnetic nanoparticles having a Curie temperature of 47° C., wherein the composition of the nanoparticles comprises an alloy of the formula $Mn_{0.5}Zn_{0.5}Fe_2O_4$ and the nanoparticles have an effective mean diameter of between 10 nm and 400 nm.

2. The composition of claim 1, further comprising a polymeric material.

3. The composition of claim 2, wherein the nanoparticles are coated by or dispersed in a biocompatible polymeric material.

4. The composition of claim 1, further comprising a drug.

5. The composition of claim 4, wherein the magnetic nanoparticles and the drug are contained in a biodegradable polymeric material.

6. The composition of claim 1, wherein the nanoparticles are made by a process comprising the steps of:

forming a melt which comprises at least two different metals;

solidifying the melt to form a bulk solid alloy of the metals;

grinding the bulk solid alloy to form particles of the alloy; and subjecting the particles to a ball milling process effective to form magnetic nanoparticles of the alloy.

7. The composition of claim 1, wherein the nanoparticles are synthesized by chemical coprecipitation process.

8. A pharmaceutical composition comprising:

magnetic nanoparticles having a Curie temperature of 47° C., wherein the composition of the nanoparticles comprises an alloy of the formula $Mn_{0.5}Zn_{0.5}Fe_2O_4$ and the nanoparticles have an effective mean diameter of between 10 nm and 400 nm; and a pharmaceutically acceptable carrier.

* * * * *